United States Patent [19]
Madhani et al.

[11] Patent Number: 5,807,377
[45] Date of Patent: Sep. 15, 1998

[54] FORCE-REFLECTING SURGICAL INSTRUMENT AND POSITIONING MECHANISM FOR PERFORMING MINIMALLY INVASIVE SURGERY WITH ENHANCED DEXTERITY AND SENSITIVITY

[75] Inventors: Akhil J. Madhani; J. Kenneth Salisbury, both of Cambridge, Mass.

[73] Assignee: Intuitive Surgical, Inc., Mountain View, Calif.

[21] Appl. No.: 858,048

[22] Filed: May 16, 1997

Related U.S. Application Data

[60] Provisional application No. 60/017,981 May 20, 1996.
[51] Int. Cl.$^6$ .............................. A61B 17/00; B25J 17/00
[52] U.S. Cl. ..................... 606/1; 74/490.01; 74/490.05; 74/490.06
[58] Field of Search ................. 606/1, 130; 74/490.01, 74/490.04, 490.05, 490.06

[56] References Cited

U.S. PATENT DOCUMENTS

| | | | |
|---|---|---|---|
| 4,762,455 | 8/1988 | Coughlan et al. | 414/4 |
| 4,921,393 | 5/1990 | Andeen et al. | 414/729 |
| 5,078,140 | 1/1992 | Kwoh | 128/653.1 |
| 5,339,799 | 8/1994 | Kami et al. | 128/4 |
| 5,368,015 | 11/1994 | Wilk | 128/4 |
| 5,528,955 | 6/1996 | Hannaford et al. | 74/490.01 |

FOREIGN PATENT DOCUMENTS

WO 97/29690  8/1997  WIPO .

OTHER PUBLICATIONS

Alexander, III, Arthur D., "Impacts of Telemation on Modern Society," *Syposium on Theory and Practice of Robots and Manipulators*, vol. II, Sept. 5–8, 1973, pp. 122–136.

Bejczy, A.K. et al., "Controlling Remote Manipulators Through Kinesthetic Coupling," *Computers in Mechanical Engineering*, pp. 48–60, Jul. 1983.

Taubes, Gary, "Surgery in cyberspace," *Discover*, pp. 85–92, Dec. 1994.

*Primary Examiner*—Michael Buiz
*Assistant Examiner*—Julian W. Woo
*Attorney, Agent, or Firm*—Townsend and Townsend and Crew LLP

[57] ABSTRACT

An articulated surgical instrument for enhancing the performance of minimally invasive surgical procedures is coupled to a positioning mechanism for supporting and moving the surgical instrument. The positioning mechanism mounts to an operating room table. The instrument has a high degree of dexterity, low friction, low inertia and good force reflection and the positioning mechanism provides a large range of motion to the instrument. The system is operated according to a macro-micro actuation scheme which allows for a large range of motion of the surgical end effector and also allows for sensitive force feedback to a master controller by reducing the measured inertia of the slave system. The macro-micro actuation scheme may be used in conjunction with impedance scaling and force scaling between the instrument and the master controller.

21 Claims, 11 Drawing Sheets

FORCE-REFLECTING SURGICAL INSTRUMENT AND POSITIONING MECHANISM FOR PERFORMING MINIMALLY INVASIVE SURGERY WITH ENHANCED DEXTERITY AND SENSITIVITY

This application claims the benefit of U.S. provisional application Ser. No. 60/017,981, filed May 20, 1996, the disclosure of which is incorporated by reference.

FIELD OF THE INVENTION

This invention relates generally to methods and apparatus for enhancing the performance of minimally invasive surgery. This invention relates particularly to surgical systems using servomechanisms to augment a surgeon's ability to perform minimally invasive surgical procedures. This invention relates more particularly to a novel combination of surgical instrument and instrument positioning system for minimally invasive surgery which has a high degree of dexterity, low friction, low inertia and good force reflection.

BACKGROUND OF THE INVENTION

Minimally invasive medical techniques are aimed at reducing the amount of extraneous tissue which must be damaged during diagnostic or surgical procedures, thereby reducing patient recovery time, discomfort, and deleterious side effects. Approximately 21,000,000 surgeries are now performed each year in the United States. It is estimated that 8,000,000 of these surgeries can potentially be performed in a minimally invasive manner. However, only about 1,000,000 surgeries currently use these techniques due to limitations in minimally invasive surgical instruments and techniques and the additional surgical training required to master them.

Advances in minimally invasive surgical technology could have a dramatic impact. The average length of a hospital stay for a standard surgery is 8 days, while the average length for the equivalent minimally invasive surgery is 4 days. Thus, the complete adoption of minimally invasive techniques could save 28,000,000 hospital days, and billions of dollars annually in hospital residency costs alone. Patient recovery times, patient discomfort, surgical side effects, and time away from work are also reduced with minimally invasive surgery.

The most common form of minimally invasive surgery is endoscopy. Probably the most common form of endoscopy is laparoscopy which is minimally-invasive inspection and surgery inside the abdominal cavity. In standard laparoscopic surgery, a patient's abdomen is insufflated with gas, and cannula sleeves are passed through small (approximately ½ inch) incisions to provide entry ports for laparoscopic surgical instruments.

The laparoscopic surgical instruments generally include a laparoscope for viewing the surgical field, and working tools such as clamps, graspers, scissors, staplers, and needle holders. The working tools are similar to those used in conventional (open) surgery, except that the working end of each tool is separated from its handle by an approximately 12-inch long extension tube.

To perform surgical procedures, the surgeon passes instruments through the cannula and manipulates them inside the abdomen by sliding them in and out through the cannula, rotating them in the cannula, levering (i.e., pivoting) the instruments in the abdominal wall and actuating end effectors on the distal end of the instruments. The instruments pivot around centers of rotation approximately defined by the incisions in the muscles of the abdominal wall. The surgeon monitors the procedure by means of a television monitor which displays the abdominal worksite image provided by the laparoscopic camera.

Similar endoscopic techniques are employed in arthroscopy, retroperitoneoscopy, pelviscopy, nephroscopy, cystoscopy, cisternoscopy, sinoscopy, hysteroscopy and urethroscopy. The common feature of all of these minimally invasive surgical techniques is that they visualize a worksite within the human body and pass specially designed surgical instruments through natural orifices or small incisions to the worksite to manipulate human tissues and organs thus avoiding the collateral trauma caused to surrounding tissues which would result from creating open surgical access.

There are many disadvantages of current minimally invasive surgical technology. First, the video image of the worksite is typically a two-dimensional video image displayed on an upright monitor somewhere in the operating room. The surgeon is deprived of three-dimensional depth cues and may have difficulty correlating hand movements with the motions of the tools displayed on the video image. Second, the instruments pivot at the point where they penetrate the body wall causing the tip of the instrument to move in the opposite direction to the surgeon's hand. Third, existing MIS instruments deny the surgeon the flexibility of tool placement found in open surgery. Most laparoscopic tools have rigid shafts and are constrained to approach the worksite from the direction of the small incision. Fourth, the length and construction of many endoscopic instruments reduces the surgeon's ability to feel forces exerted by tissues and organs on the end effector of the tool.

Overcoming these disadvantages and achieving expertise in endoscopic procedures requires extensive practice and constant familiarization with endoscopic tools. However, despite surgeon's adaptation to the limitations of endoscopic surgery the technique has brought with it an increase in complications seldom seen in open surgery such as bowel perforations due to trocar or cautery injuries. Moreover, one of the biggest impediments to the expansion of minimally invasive medical practice remains lack of dexterity of the surgical tools and the difficulty of using the tools.

Telesurgery systems for use in surgery are being developed to increase a surgeon's dexterity as well as to allow a surgeon to operate on a patient from a remote location. Telesurgery is a general term for surgical systems where the surgeon indirect controls surgical instrument movements rather than directly holding and moving the tools. In a system for telesurgery, the surgeon is provided with an image of the patient's body at the remote location. While viewing the three-dimensional image, the surgeon performs the surgical procedures on the patient by manipulating a master device which controls the motion of a servomechanism-actuated instrument. The surgeon's hands and the master device are positioned relative to the image of the operation site in the same orientation as the instrument is positioned relative to the act. During the operation, the instrument provides mechanical actuation and control of a variety of surgical instruments, such as tissue graspers, needle drivers, etc., that each perform various functions for the surgeon, i.e., holding or driving a needle, grasping a blood vessel or dissecting tissue.

Such telesurgery systems have been proposed for both open and endoscopic procedures. An overview of the state of the art with respect to telesurgery technology can be found in "Computer Integrated Surgery: Technology And Clinical Applications" (MIT Press, 1996). Moreover, prior systems for telesurgery are described in U.S. Pat. Nos. 5,417,210, 5,402,801, 5,397,323, 5,445,166, 5,279,309, 5,299,288.

Proposed methods of performing telesurgery using telemanipulators create many new challenges. One such challenge is transmitting position, force, and tactile sensations from the surgical instrument back to the surgeon's hands as he/she operates the telesurgery system such that the surgeon has the same feeling as if manipulating the surgical instruments directly by hand. For example, when the instrument engages a tissue structure or organ within the patient, the system should be capable of detecting the reaction force against the instrument and transmitting this force to the surgeon. Providing the instrument with force reflection is required to reduce the likelihood of accidentally damaging tissue in areas surrounding the operation site. Force reflection enables the surgeon to feel resistance to movements of the instrument when the instrument engages tissue.

A system's ability to provide force reflection is limited by factors such as friction within the mechanisms, gravity, the inertia of the surgical instrument and forces exerted on the instrument at the surgical incision. Even when force sensors are used, inertia, friction and compliance between the motors and force sensors decreases the quality of force reflection provided to the surgeon.

Another challenge is that, to enable effective telesurgery, the instrument must be highly responsive and must be able to accurately follow the rapid hand movements that a surgeon may use in performing surgical procedures. To achieve this rapid responsive performance, a surgical servomechanism system must be designed to have an appropriately high servo bandwidth. This requires that the instrument be designed to have low inertia and to employ drive motors with relatively low ratio gear or pulley couplings. It is also preferable if the system can enhance the dexterity of the surgeon compared to standard endoscopic techniques by providing more degrees-of-freedom to perform the surgery by means of an easily controlled mechanism.

Another challenge is that to enable minimally invasive surgery, the instrument must be small and compact in order to pass through a small incision. Typically MIS procedures are performed through cannulas ranging from 5 mm to 12 mm in diameter.

What is needed, therefore, is an servomechanical surgical apparatus for holding and manipulating human tissue under control of a teleoperator system.

It would also be desirable to provide a servomechanical surgical apparatus which can provide the surgeon with sensitive feedback of forces exerted on the surgical instrument.

It would further be desirable to provide a servomechanical surgical apparatus which compensates for gravitational forces acting on the apparatus and ensures these forces are not felt by the surgeon.

It would further be desirable to provide a servomechanical surgical apparatus which is highly responsive, has a large range of motion and can accurately follow rapid hand motions that a surgeon frequently uses in performing surgical procedures.

It would still further be desirable to provide a servomechanical surgical apparatus that increases the dexterity with which a surgeon can perform endoscopic surgery by providing an easily controlled wrist joint.

SUMMARY AND OBJECTS OF THE INVENTION

It is accordingly an object of this invention to provide a servomechanical surgical apparatus for holding and manipulating human tissue under control of a teleoperator system.

It is also an object of this invention to provide a servomechanical surgical apparatus which can provide the surgeon with sensitive feedback of forces exerted on the surgical instrument.

It is a further object of this invention to provide a servomechanical surgical apparatus which compensates for gravitational forces acting on the apparatus and ensures these forces are not felt by the surgeon.

It is a further object of this invention to provide a servomechanical surgical apparatus which is highly responsive, has a large range of motion and can accurately follow rapid hand motions that a surgeon frequently uses in performing surgical procedures.

It is still further an object of this invention to provide a servomechanical surgical apparatus that increases the dexterity with which a surgeon can perform endoscopic surgery by providing an easily controlled wrist joint.

In accordance with the above objects of the invention applicants describe a servomechanical system including a compact servomechanism-operated surgical instrument suitable for endoscopic surgery. The instrument has two opposed pivoting jaws and may have a pivoting wrist member. The instrument is adapted to be coupled via the servomechanism to a master control operated by a surgeon. The instrument and wrist member when combined with the servomechanical system are capable of providing four degrees of force reflection with high sensitivity. The instrument is mounted on a positioning mechanism which operates to move the instrument with two degrees-of-freedom over a wide range of motion. A macro-micro actuation and control system eliminates the effects of gravity, inertia and other extraneous forces acting on the positioning mechanism from the forces reflected to the surgeon.

BRIEF DESCRIPTION OF THE DRAWINGS

The foregoing and other objects, features and advantages of the invention will be apparent from the following more particular description of preferred embodiments of the drawings in which like reference characters refer to the same parts throughout the different views. The drawings are not necessarily to scale, emphasis instead being placed upon illustrating the principles of the invention.

DETAILED DESCRIPTION OF THE PREFERRED EMBODIMENTS

Figure 1:
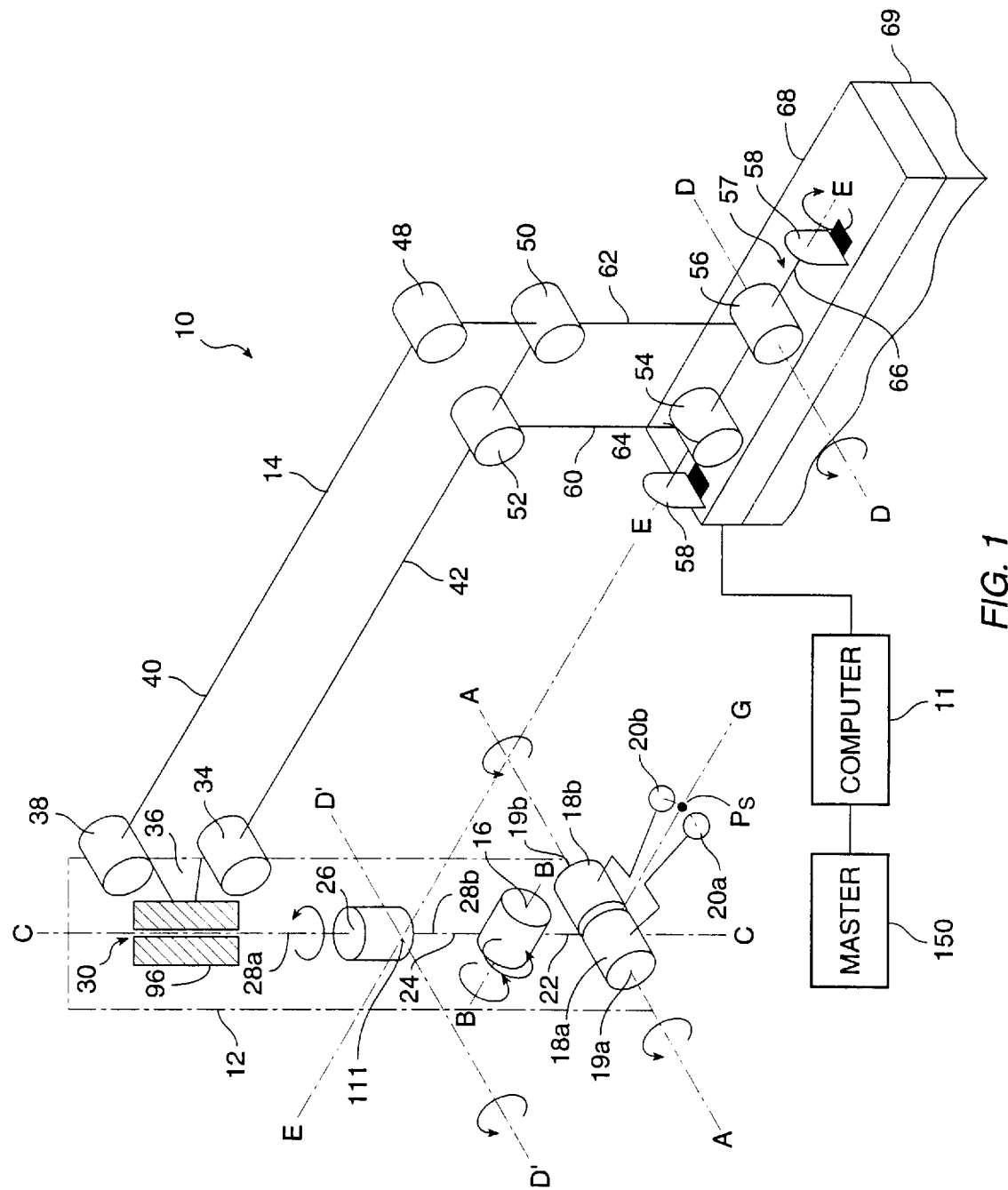
FIG. 1 is a schematic drawing of the servomechanical surgery system including a force-reflecting instrument mounted to a positioning mechanism.

The instrument in the first embodiment includes an elongate support member having a proximal portion and a distal portion lying along a longitudinal axis. A distal wrist member is rotatably coupled to the distal portion of the support member by a wrist joint. First and second opposed work members are mounted to respective first and second driven capstans. The first and second driven capstans are rotatably mounted to the wrist member by respective first and second capstan joints. First, second, third and fourth intermediate idler pulleys are rotatably mounted to the wrist member about the wrist joint. A cable drive system including first, second, third and fourth cables is provided. Each intermediate idler pulley is engaged by one cable and each driven capstan is drivingly engaged by two cables. The cable drive system is capable of pivoting the wrist member about the wrist joint and pivoting the work members independently of each other about the capstan joints.

In preferred embodiments, the first and second capstan joints lie along a common axis. The instrument further includes first, second, third and fourth actuators, each for driving respective first, second, third and fourth cables. When all four actuators are actuated, the cable drive system is capable of translating the support member along the longitudinal axis.

First and second proximal idler pulleys engage and tension the first through fourth cables. In addition, fifth and sixth cables are connected to the first and second proximal idler pulleys. A third proximal idler pulley is rotatably mounted to the proximal portion of the support member for engaging and tensioning the fifth and sixth cables, thereby tensioning the first and second proximal idler pulleys and the first through fourth cables. The actuators are preferably drive motors which are positioned between the intermediate idler pulleys and the proximal idler pulleys.

The support member further includes a rotary joint separating the proximal and distal portions of the support member for allowing rotation of the distal portion relative to the proximal portion about the longitudinal axis. A fifth actuator is coupled to the distal portion of the support member by a seventh cable for rotating the distal portion about the longitudinal axis. The first through fourth cables are capable of twisting about the longitudinal axis during rotation of the distal portion.

The instrument is a slave device which is controlled by a master device and a controller. Movements of the instrument and the master device as well as forces exerted thereon may be scaled between the instrument and the master device. A four bar linkage positioning mechanism having two degrees-of-freedom is mounted to the instrument for positioning the instrument over a work site. The positioning mechanism provides the instrument with redundant degrees-of-freedom for positioning the endpoint. The combination of the positioning mechanism with the instrument enables a user operating the master device to feel forces that are experienced by the instrument during positioning and use of the instrument with greater sensitivity than with prior systems.

The present invention also provides a cable drive system for driving an instrument including first, second, third and fourth cables for driving the instrument. A first proximal idler pulley rotatably engages and tensions the first and second cables. A second proximal idler pulley rotatably engages and tensions the third and fourth cables. Fifth and sixth cables are connected to the first and second proximal idler pulleys for tensioning the first and second proximal idler pulleys. A third more proximal idler pulley is rotatably mounted to a support member for rotatably engaging and tensioning the fifth and sixth cables. First, second and third actuators are included with each actuator driving one of the first to sixth cables.

In preferred embodiments, a linear bearing is mounted in sliding engagement with the support member for allowing the support member to be reciprocated relative to the linear bearing. The cable drive system further includes a fourth actuator so that each of the first to fourth actuators drives one of the first to sixth cables.

Details about the preferred attributes of the surgical instrument are also described in applicants' copending applications titled "Wrist Mechanism For Surgical Instrument For Performing Minimally Invasive Surgery With Enhanced Dexterity And Sensitivity" and "Articulated Surgical Instrument For Performing Minimally Invasive Surgery With Enhanced Dexterity And Sensitivity" filed on even date herewith. The disclosures of these applications are incorporated herein by reference.

Referring to FIG. 1, telesurgery system 10 allows a surgeon at one location to perform surgery on a patient at another location. The surgeon may be in the same operating room as the patient or many miles away. Telesurgery system 10 includes a force-reflecting surgical instrument 12 which is mounted by a mounting bracket 36 to a positioning mechanism 14. Instrument 12 and positioning mechanism 14 are controlled by a computer 11 and a master device 150 which is manipulated by a surgeon at a remote location. Instrument 12 and positioning mechanism 14 are driven by drive motors M1, M2, M3, M4, M5, M6 and M7 (FIGS. 4a, 4b, 6 and 7) in conjunction with a series of cables and pulleys.

Instrument 12 has low friction, low inertia and high bandwidth but a small range of motion. Positioning mechanism 14 has a large range of motion but has a higher inertia and a lower bandwidth than the instrument 12. The combination of instrument 12 and positioning mechanism 14 in a macro-micro actuation scheme results in a system with enhanced manipulation and force sensing capabilities compared to either of its individual components. Positioning mechanism 14 provides telesurgery system 10 with redundant degrees-of-freedom and helps position instrument 12 at a surgical worksite so that instrument 12 is generally in the proper location for performing the necessary surgery. Thus, by mounting instrument 12 on positioning mechanism 14, telesurgery system 10 is provided with high quality force control through the use of instrument 12 while at the same time having a large range of motion due to positioning mechanism 14.

Instrument 12 has a proximal portion 28a which is rotatably coupled to a distal portion 28b by a rotary joint 26. Proximal portion 28a is slidably coupled to a sliding bracket 96 which forms a sliding joint 30. Sliding bracket 96 is fixed to bracket 36. Distal portion 28b includes a wrist member which is rotatably coupled to a tubular support member 24 by a wrist joint 16. Two opposed work members 20a and 20b are fixed to respective driven capstans 18a and 18b which are rotatably coupled to wrist member 22 about capstan joints 19a and 19b. The work members 20a and 20b can be the operative end of standard surgical instruments such as scissors, retractors, needle drivers and electrocautery instruments.

Instrument 12 has five degrees-of-freedom with sliding joint 30 providing linear motion along longitudinal axis C, rotary joint 26 providing rotational motion about axis C, wrist joint 16 providing rotational motion about axis B and capstan joints 19a and 19b providing rotational motion about axis A for work members 20a and 20b. Instrument 12 provides master device 150 with four degrees of force reflection so that the surgeon can have tactile feedback of surgical procedures. These degrees of force reflection include forces exerted on the work members 20a and 20b, as well as the holding force between work members 20a and 20b. However, force reflection can be provided on more or less motion axes as required in any particular embodiment.

Positioning mechanism 14 is a two degree-of-freedom linkage consisting of a four bar linkage which rotates about an axis E—E. Positioning mechanism 14 has a series of rigid members 36, 40, 42, 60 and 62 which are joined together by joints 34, 38, 48, 50, 52, 54, 56. Positioning mechanism 14 also includes a base 68 having ears 58 which engage shafts 64 and 66 to form a joint 57 for pivoting about axis E—E. Joint 56 allows link 62 to rotate about axis D—D which is orthogonal to axis E—E. The four bar linkage of rigid members 36, 40, 42, 60 and 62 transmits this rotation to instrument 12 via bracket 36 causing instrument 12 to rotate about axis E—E and axis D'—D' (axis D'—D' is parallel to axis D—D and intersects axis E—E orthogonally). Thus the four bar linkage operates to move point $P_s$ of instrument 12 about the surface of a sphere having its center at a remote center 111.

Although a four bar linkage has been shown, the present invention can incorporate any suitable positioning mechanism. To be suitable for minimally invasive surgery the positioning mechanism must pivot the surgical instrument about axes that intersect at the orifice through which the instrument 12 is inserted into the patient. One of the advantages of the present invention is that it does not require force feedback information to be provided by the positioning mechanism and thus allows a wide range of positioning mechanism design.

Figure 2:
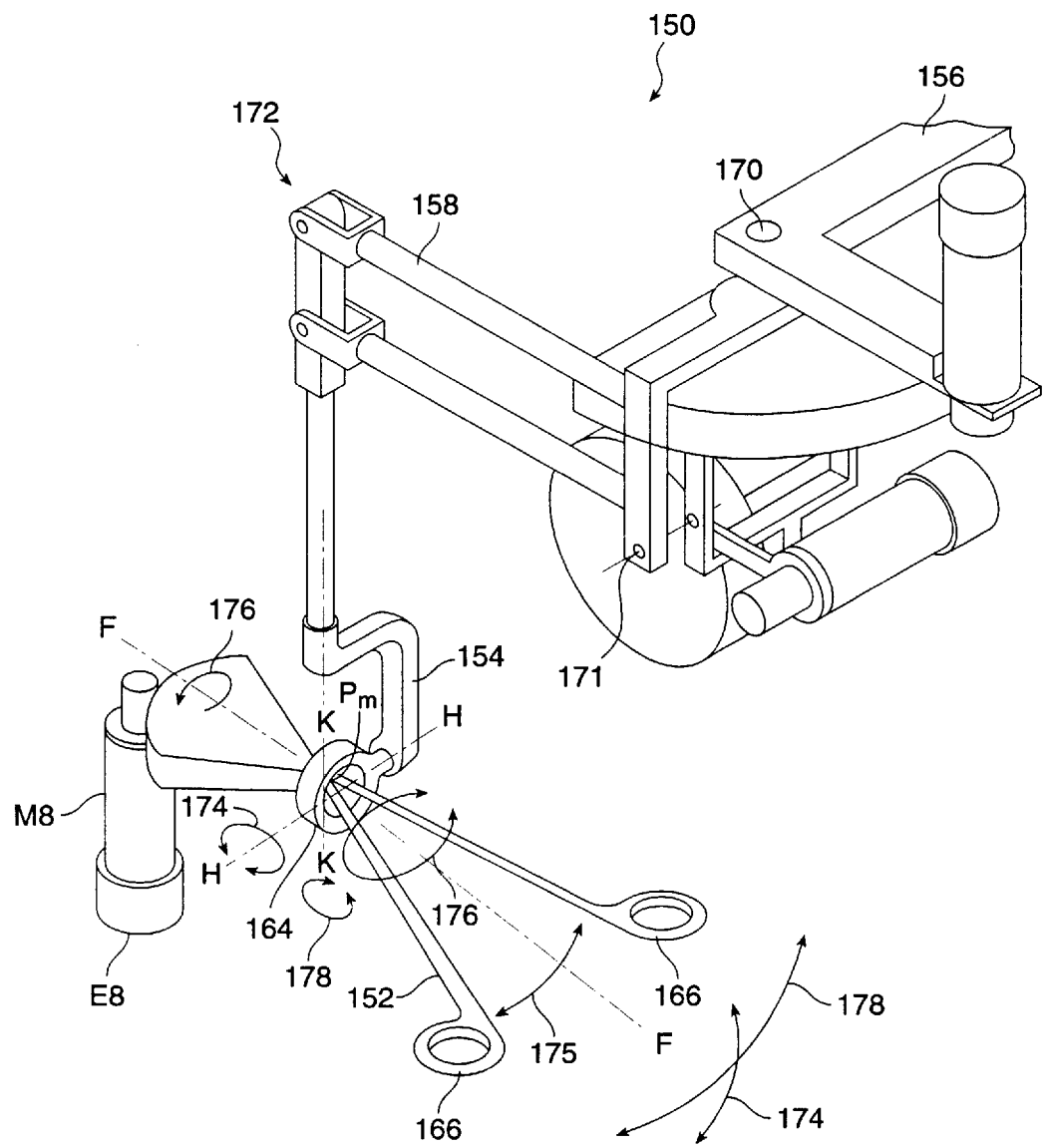
FIG. 2 is a perspective view of a preferred master device for controlling the force-reflecting surgical instrument and positioning mechanism.

Referring to FIG. 2, a simplified illustration of a haptic master device 150 suitable to control instrument 12 and positioning mechanism 14 is shown. Master device 150 includes a two degree-of-freedom linkage 158 which is pivotably coupled to a mount 156 (partially shown). During use, the mount 156 is fixed in place to a console or cart or similar stationary support such that the mount provides a fixed reference point. Linkage 158 includes rotary joints 170, 171 and 172. A work member control mechanism 152 is coupled to the distal end 154 of linkage 158 by a gimbal joint 164. Master device 150 also includes a series of encoders (not shown) which provide computer 11 with the rotational position of each joint in order to control the drive motors of instrument 12 and positioning mechanism 14.

During use, the surgeon inserts his/her thumb and forefinger into the finger grips 166 of work member control mechanism 152 for manipulating the position and orientation of mechanism 152 relative to mount 156. This controls motions of instrument 12 and positioning mechanism 14 for controlling the position of the distal end of instrument 12 relative to the surgical site.

Mechanism 152 of master device 150 has three translational degrees-of-freedom along axes F—F, H—H and K—K. Rotation of joints 170, 171 and 172 of master device 150 determine the position of a point $P_m$ on mechanism 152 which is centered within gimbal joint 164. The position of point $P_m$ controls the position of a point $P_s$ (see FIGS. 1, 4 and 5) which is located midway along an arc connecting work members 20a and 20b. Thus translation of point $P_m$ along the axes F—F, H—H and K—K by the surgeon in manipulating mechanism 152 is detected by the encoders of joints 170, 171 and 172. The information from the encoders is fed to computer 11 which controls the appropriate currents to the motors of the positioning mechanism 14 and instrument to cause corresponding motion of point PS of the instrument.

Mechanism 152 of master device 150 additionally has three rotational degrees-of-freedom about axes F—F, H—H and K—K. Rotating ring grips 166 of mechanism 152 relative to gimbal joint 164 about axis F—F as indicated by arrow 176 controls the net rotation of work members 20a and 20b of instrument 12 about axis G (FIGS. 1, 4 and 5). Axis G is an axis which extends from wrist member 22 perpendicularly to axis A and between work members 20a and 20b. The net rotation of work members 20a and 20b about axis G requires coordinated rotation of the instrument elements about axis A—A and B—B. Computer 11 determines the appropriate transformation from master rotation to instrument rotation according to standard methods. Likewise, rotating mechanism 152 about axis K—K as indicated by arrow 178 or about axis H—H as indicated by arrow 174 also causes coordinated motion of instrument 12 about axes A—A, B—B and C—C to cause corresponding rotational movement of the work members of the instrument.

Mechanism 152 has a seventh degree-of-freedom in that finger grips 166 can be moved together and apart as indicated by arrow 175. Relative motion of finger grips 166 is detected by encoder E8 of motor M8. Position data is transmitted from encoder E8 to computer 11. Computer E8 then transmits the appropriate signals to motors M1–M4 of instrument 12 to cause corresponding relative motion of capstan joints 19a and 19b and work members 20a and 20b.

Although the work member control mechanism 152 may comprise typical surgical instrument handles as shown in FIG. 2 it could alternatively comprise thimbles or similar devices which can be operated by the surgeon's fingers. As an alternative embodiment work member control mechanism 152 can be replaced by a simple wand connected to gimbal joint 164 for orientating instrument 12. One apparatus suitable for use as a master in the presently described system is described in U.S. Pat. No. 5,587,937, titled Force Reflecting Haptic Interface the contents of which are incorporated by reference herein. Another suitable master device is described in U.S. Pat. No. 5,576,727, titled Electromechanical Human-Computer Interface With Force-Feedback the contents of which are incorporated by reference herein. For use in this invention, the apparatus disclosed in the above references would require the addition of a further powered degree-of-freedom to provide force reflection from gripping the work members. Potentially, in this embodiment finger grippers 166 motor M8 and encoder E8 may be located on a separate mechanism for operation by the other hand of the surgeon. Alternatively, finger grippers may be attached to a motor and encoder on the same device for operation by the surgeon.

When employing telesurgery system 10 for laparoscopic surgery, positioning mechanism 14 is mounted to a manually-operated setup joint (not shown). This setup joint may be mounted to a surgical cart which is fixed in place relative to the patient. The setup joint may also be used to mount the positioning mechanism 14 directly on to a rail affixed to the operating table. In a third alternative, the set-up joint may be permanently mounted in the operating room either to the floor, a wall or the ceiling. The common feature of all the setup joints is that they permit the base of the positioning arm to be moved relative to the patient during setup for the surgical procedure and allow the arm to be located so that the point 111 is at the appropriate entry point on the patient over the approximate location of the surgical site. Preferably the setup joint would have six degrees-of-freedom thus allowing translation and rotation of position mechanism 14 relative to the patient. Typically the setup joint would be locked in position during the procedure to movement of the remote center point 111 relative to the patient.

Figure 3:
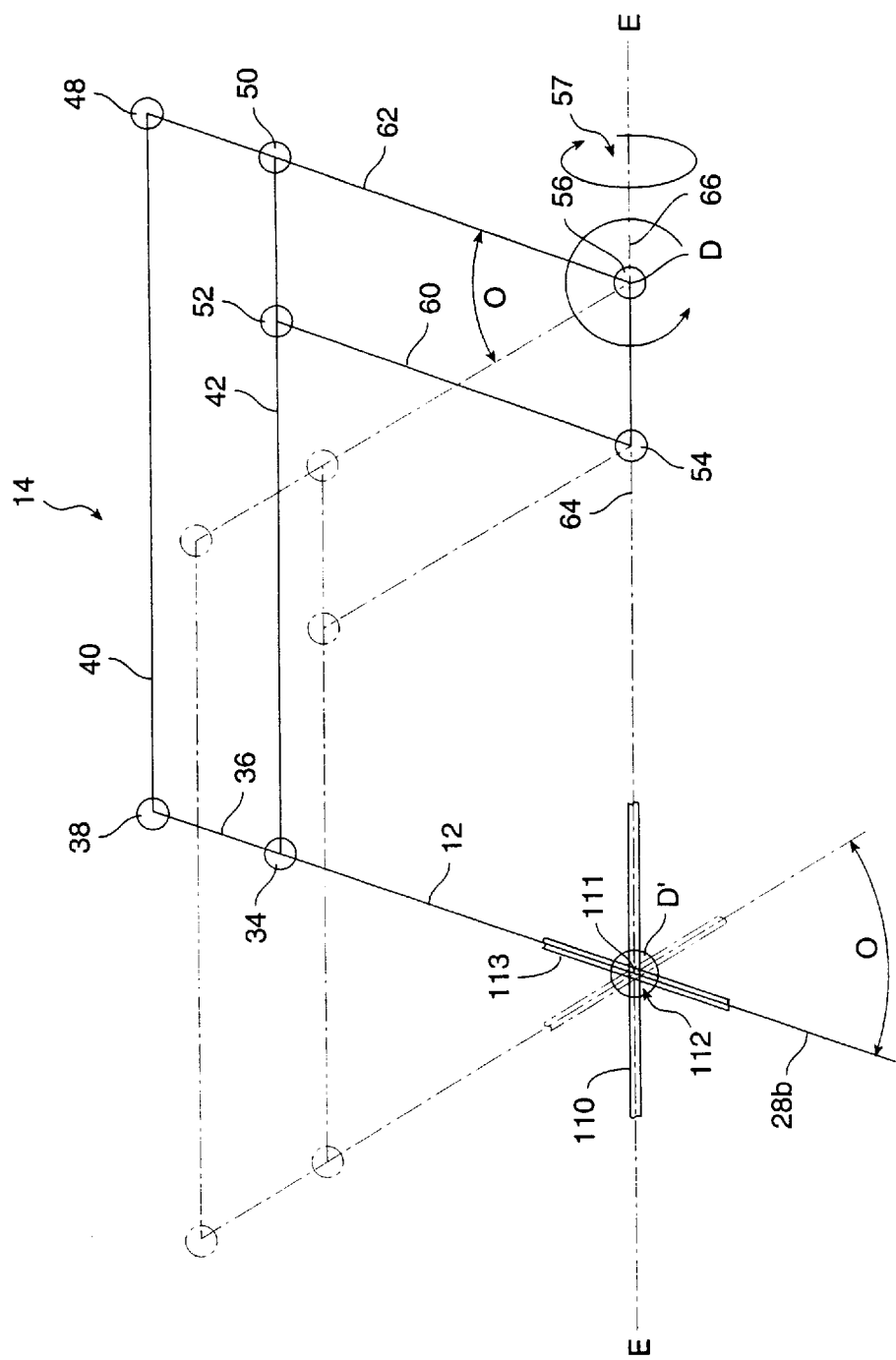
FIG. 3 is a schematic drawing of the positioning mechanism in forward and rearward positions with the instrument inserted into a patient.

Referring to FIG. 3, after the setup joint has been used to position the tool and lock the tool in place, the surgeon then manipulates master device 150 to move instrument 12 through a cannula 113 inserted through small incision 112 in the abdominal wall 110 of the patient. In response to manipulation of master device 150, the distal portion 28b of the instrument 12 is translated downwardly relative to positioning mechanism 14 along sliding joint 30 for insertion through cannula 113 and abdominal wall 110. Once within the abdomen, the distal portion 28b of instrument is further positioned over the desired surgical site. FIG. 3 depicts motion of mechanism 14 pivoted about axis D—D in forward and rearward positions for making large position movements. Positioning mechanism 14 pivots about axes D and E to perform large movements of telesurgery system 10 while precise movements are made by the joints of instrument 12. Point 111 on instrument 12 is a remote point of rotation from positioning mechanism 14 which coincides with entry wound 112. When positioning mechanism 14 is pivoted about axes D and E, instrument 12 pivots about point 111. Note that point 111 adjacent incision 112 remains stationary as the instrument 12 is pivoted within the patient. As a result, incision 112 only needs to be large enough to accept instrument 12.

As positioning mechanism 14 pivots, if wrist member 22 or work members 20a/20b engage tissue causing rotation about joints 16 or 19a/19b, instrument 12 will reorient itself so that instrument 12 is maintained relative to positioning mechanism 14 in the middle of its workspace. If necessary, positioning mechanism 14 can slow down as instrument 12 is reorienting itself.

Once instrument 12 is in the proper position, by further manipulating master device 150, the surgeon can perform the necessary surgical procedures on the patient with instrument 12. Forces experienced by instrument 12 are reflected back to the surgeon by master device 150. The reflected forces may be scaled up in order to allow the surgeon to better "feel" the surgical procedures. As a result, the surgeon can feel instrument 12 engaging types of tissue that do not provide much resistance. In addition, movements of master device 150 relative to instrument 12 may be scaled down so that the precision and dexterity of instrument 12 can be increased.

Positioning mechanism 14, because it is optimized to have a large range of motion, is likely to have higher inertia, higher friction and lower resolution than instrument 12. Moreover, friction forces in cannula 113 and disturbance forces at incision 112 may be applied to the positioning mechanism. However, in applicants' preferred embodiment, it is primarily the instrument that detects forces for force reflection. Therefore, the higher inertia and friction of the positioning mechanism and the extraneous forces acting on it are excluded from the force reflection system. Thus, the quality of the force reflection between the tip of the instrument 12 and the master device is greatly improved.

Figure 4A:
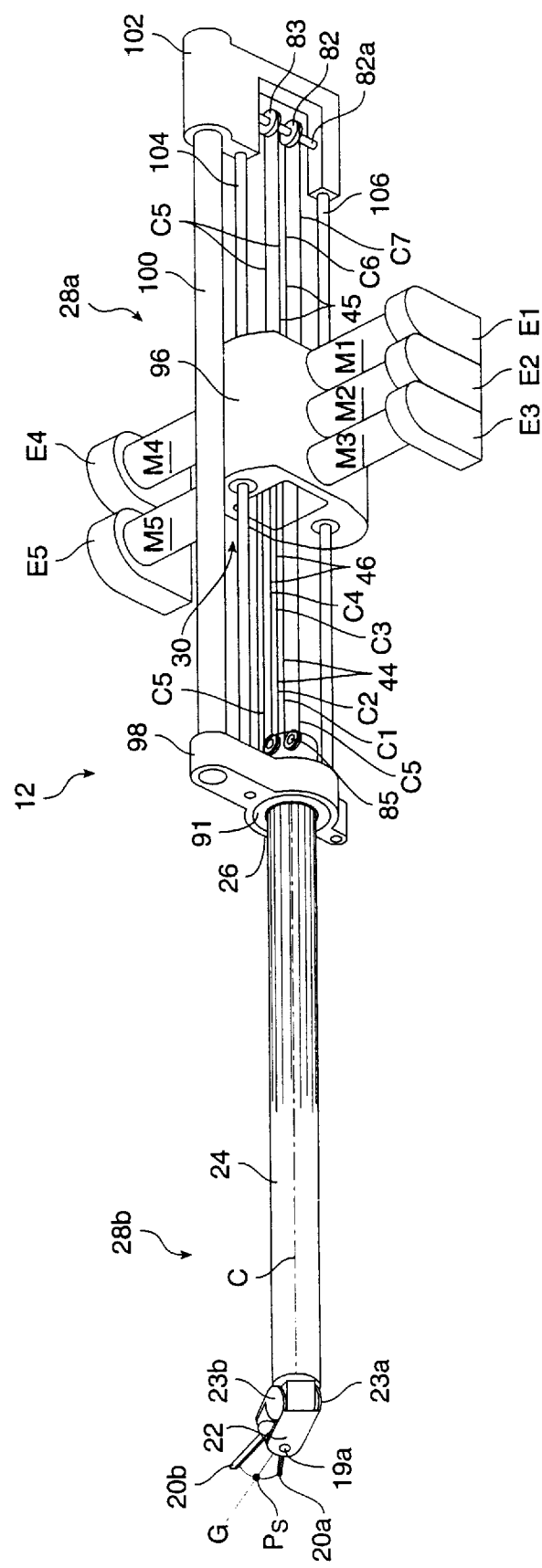
FIG. 4a is a perspective view of the force-reflecting surgical instrument.
Figure 4B:
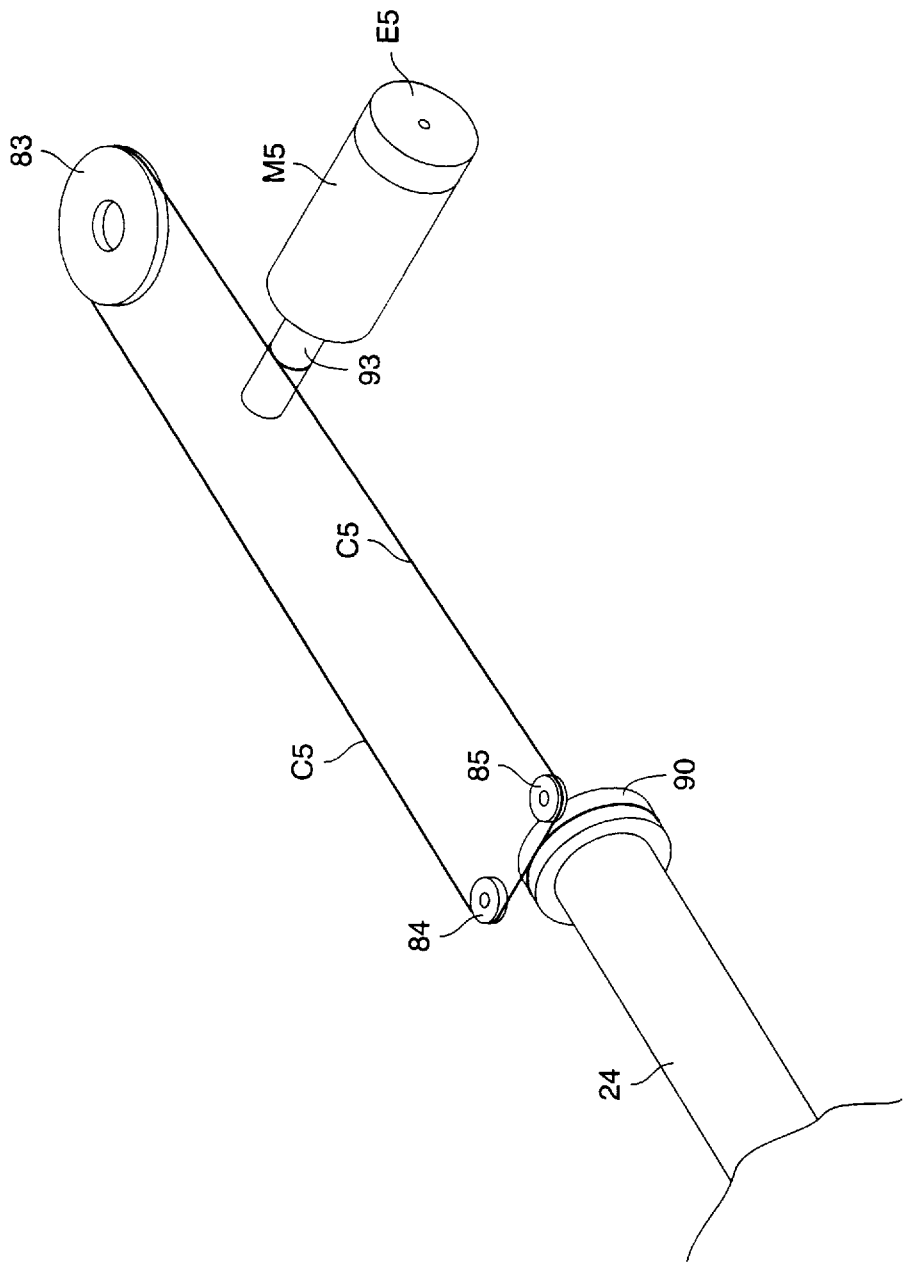
FIG. 4b is a schematic view of the cable drive actuation of the rotary motion of the instrument.
Figure 5:
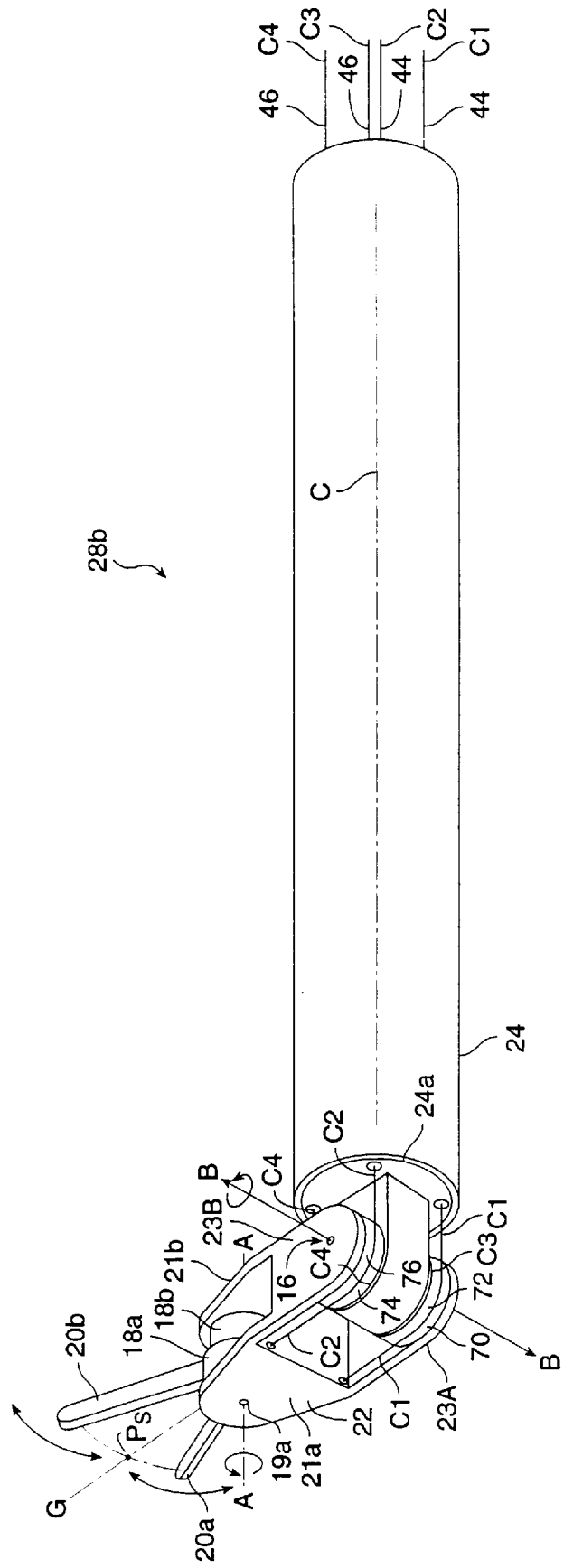
FIG. 5 is a perspective view of the distal end of the force-reflecting instrument.

Referring to FIGS. 4A, 4B and 5, instrument 12 is now described in greater detail. Tubular support member 24 of distal portion lies along axis C and houses a series of cables C1, C2, C3 and C4 which travel the length of tubular support member 24. Cables C1, C2, C3 and C4 control the rotation of joints 19a, 19b and 16 for controlling the operation of work members 20a and 20b and the orientation of wrist member 22. Wrist member 22 includes two opposed distal ears 21a and 21b which form a clevis for supporting driven capstans 18a and 18b at respective capstan joints 19a and 19b which lie along axis A—A. Wrist member 22 also includes two opposed proximal ears 23a and 23b which form a clevis for supporting intermediate idler pulleys 70 and 72 which lie along axis B—B between ear 23a and tongue 24a at wrist joint 16. Intermediate idler pulleys 74 and 76 are supported between ear 23b and tongue 24a. Cables C1, C2, C3 and C4 engage driven capstans 18a/18b as well as intermediate idler pulleys 70, 72, 74 and 76 as described later in greater detail.

Work members 20a and 20b may be removably fixed to respective driven capstans 18a and 18b. Although work members 20a and 20b are depicted in the figures as being grippers, work members 20a and 20b can be replaced with other types of work members such as scissors, cutters, graspers, forceps or needle holders for stitching sutures. Typically, the work members are fixed to driven capstans 18a and 18b by a screw, clip or other suitable fastener. However, the work members may also be permanently affixed to the driven capstans by soldering or welding or the like or may be formed in one piece with the driven capstans.

Work members 20a and 20b together comprise one form of surgical end effector. Other surgical end effectors may be used in the surgical instrument of the present invention. End effectors simply may comprise standard surgical or endoscopic instruments with their handles removed including, for example, retractors, electrocautery instruments, microforceps, microneedle holders, dissecting scissors, blades, irrigators, and sutures. The end effectors will typically comprise one or two work members.

Proximal portion 28a of instrument 12 includes support brackets 98 and 102 which are connected together by a support rod 100 as well as two guide rails 104 and 106. A rotary bearing 91 forming rotary joint 26 is housed within support bracket 98 for supporting tubular support member 24. Sliding bracket 96 is slidably mounted to guide rails 104 and 106 along linear bearings. As shown in FIG. 1, sliding bracket 96 is connected by bracket 36 to positioning mechanism 14. Sliding bracket 96 preferably has about 8 inches of travel for surgical applications. Drive motors M1, M2, M3, M4 and M5 are mounted to sliding bracket 96 and drive respective cables C1, C2, C3 and C4 and C5. Each drive motor M1, M2, M3, M4 and M5 includes a respective encoder E1, E2, E3, E4 and E5 for providing computer 11 with the rotational position of their respective drive shafts.

As shown in FIGS. 4a and 4b, drive motor M5 has a drive shaft capstan 93 which engages a cable drive loop consisting of Cable C5. The cable passes around rear tensioning pulley 83. The cable passes around idler pulleys 84 and 85 and around drive capstan 90 which forms the proximal end of tubular support member 24. Thus, actuation of motor M5 can be used to rotate tubular support member 24 and the end effector it supports.

Figure 6:
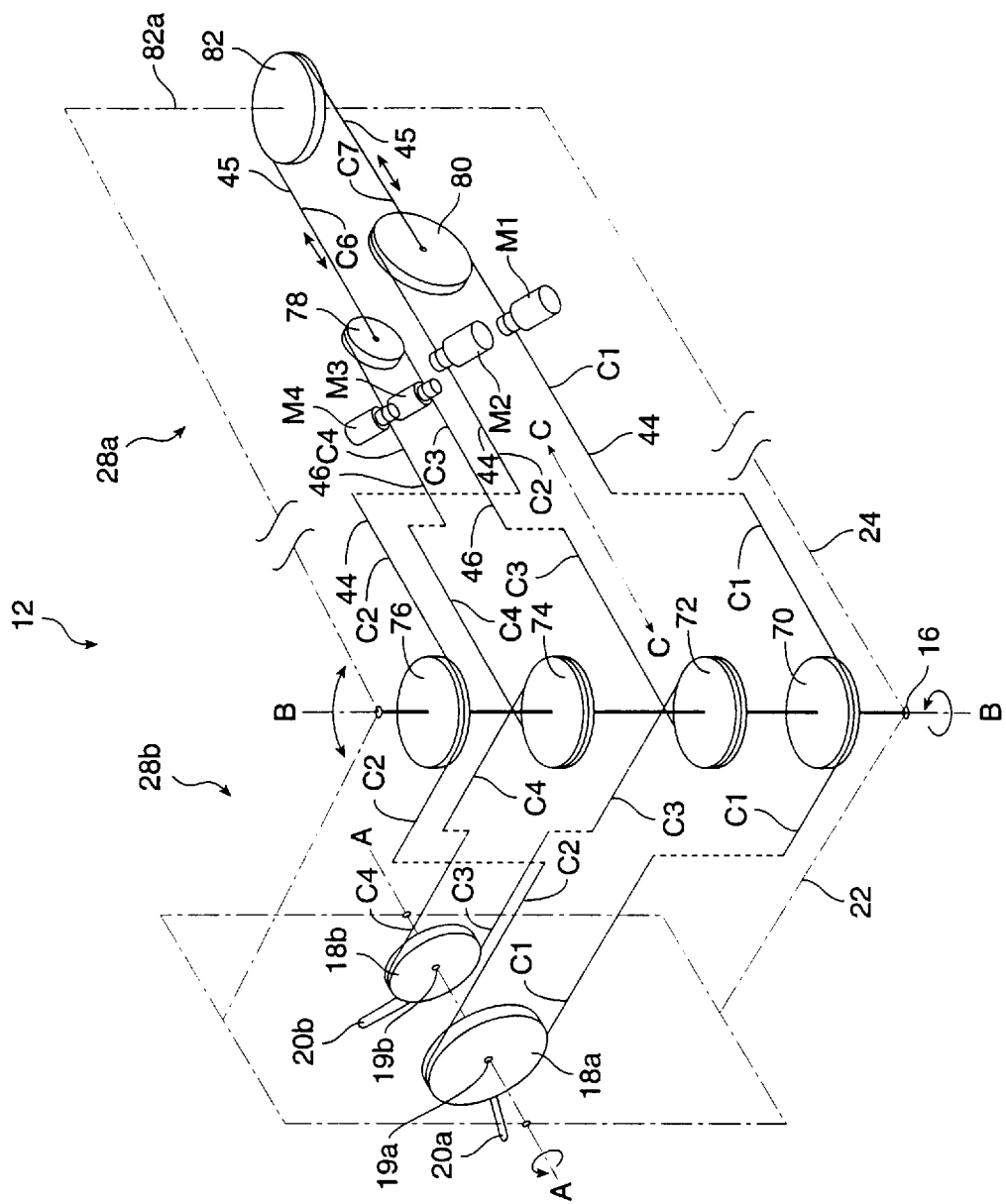
FIG. 6 is a simplified schematic drawing of the force-reflecting instrument showing the cables and pulleys.

Referring to FIG. 6, the cable drive system of instrument 12 is now described in greater detail. Work members 20a and 20b, wrist member 22 and the translation of instrument 12 along longitudinal axis C are driven by cables C1, C2, C3 and C4 which are arranged in an N+1 actuation scheme. The N+1 actuation scheme allows the actuation of a three degree-of-freedom wrist using 4 cables. 4 cables is the theoretical minimum possible number of tension elements required to drive three degrees-of-freedom and thus allows the instrument to be of minimum size and weight. Alternative actuation schemes using more cables may be desirable in situations where the forces required for actuation of different motions differ greatly in magnitude. The disadvantage of using more cables is an increase in weight, complexity and minimum size.

In FIG. 6, the rotational motion of joint 26 about axis C—C is omitted in order to more easily show cables C1–C4. Such rotation results only in twisting of the cables C1–C4 between motors M1–M4 and pulleys 70, 72, 74 and 76. The cables are however arranged in tubular support member 24 such that this twisting does not significantly change the length of the cable path. Care should however be taken to prevent over-rotation of the instrument which would cause the cables to twist into contact with each other and create friction between the cables.

As shown in FIG. 6, cables C1 and C2 form two sides of a continuous cable loop 44. Cable C1 of loop 44 engages a proximal idler pulley 80, the drive shaft of motor M1, intermediate idler pulley 70 and driven capstan 18a. Cable loop 44 returns from driven capstan 18a as cable C2 and engages intermediate idler pulley 76, the drive shaft of motor M2 and proximal idler pulley 80.

As shown in FIG. 6, cables C3 and C4 form two sides of a continuous loop of cable 46. Cable C3 of cable loop 46 engages proximal idler pulley 78, the drive shaft of motor M3, intermediate idler pulley 72 and driven capstan 18b. Cable loop 46 returns from driven capstan 18b as cable C4 and engages intermediate idler pulley 74, the drive shaft of motor M4 and proximal idler pulley 78.

As shown in FIG. 6, proximal idler pulleys 78 and 80 are tensioned by cables C7 and C6 which are fixed to the center of proximal idler pulleys 78 and 80. Cables C7 and C6 form two sides of a single cable 45 which engages proximal idler pulley 82 which is rotatably mounted to support bracket 102 by shaft 82a. Shaft 82a is preferably movably mounted to support bracket 102 by a mechanism such as a lead screw. The lead screw may then be adjusted to appropriately tension cables C7 and C6. The tension is also applied via idler pulleys 78 and 80 to cables C1, C2, C3 and C4. A similar lead screw tensioning scheme can be used to tension cable C5 by longitudinal movement of idler pulley 83. It may be required for idler pulleys 82 and 83 to be mounted on separately adjustable shafts for these purpose instead of single shaft 82a illustrated in FIG. 3.

Driven capstans 18a and 18b may have different diameters in order to allow cables C1 through C4 to suitably engage their respective intermediate idler pulleys. Cables C1 and C2 engage the outer intermediate idler pulleys 70 and 76 while cables C3 and C4 engage the inner intermediate idler pulleys 72 and 74. Proximal idler pulleys 78 and 80 are sized such that pulley 80 is larger than pulley 78 to keep the cables straight.

Drive motors M1, M2, M3 and M4 control rotation of wrist member 22 about axis B—B, translation of instrument 12 longitudinally along axis C—C and rotation of work members 22a and 22b independent of each other about axis A—A by driving cables C1, C2, C3 and C4. Drive motors M1 and M2 drive cables C1/C2 in unison in opposition to cables C3/C4 driven by drive motors M3 and M4 in order to rotate wrist member 22 about axis B—B. Drive motor M1 drives cable C1 in opposition to cable C2 driven by drive motor M2 to rotate capstan 18a and attached work member 20a about axis A—A. In addition, drive motor M3 drives cable C3 in opposition to cable C4 driven by drive motor M4 to rotate capstan 18b and attached work member 20b about axis A—A. All four drive motors M1, M2, M3 and M4 drive cables C1, C2, C3 and C4 simultaneously to translate instrument 12 along longitudinal axis C—C.

Locating drive motors M1, M2, M3, M4 and M5 on sliding bracket 96 makes the distal portion 28b of instrument 12 have a small moving mass since the motors themselves remain stationary during actuation of the instrument. Although the motors are moved by positioning mechanism 14, the weight and inertia of the motors do not affect force reflection. This is because, as stated above, in the preferred embodiment, only the instrument 12 is used to reflect forces to the master. In addition, employing cables instead of gears to control instrument 12 minimizes the amount of friction and backlash within instrument 12. The combination of small moving masses and low friction enables instrument 12 to provide force reflection to master device 150 with high sensitivity.

Certain possible changes to the configuration of pulleys, cables and motors described above will be apparent to those of skill in the art. Although cables C1/C2, C3/C4, C5 and C7/C6 have been depicted to be sides of the same cables, cables C1–C7 alternatively can each be individual cables which are fixed to driven capstans 18a and 18b, and proximal idler pulleys 78, 80 and 82. Moreover, although drive motors M1, M2, M3 and M4 have been depicted to drive cables C1, C2, C3 and C4 respectively, alternatively, some drive motors can be relocated from cables C1–C4 onto cables C7 and C6 for driving cables C7 and C6. The choice of the particular drive scheme employed in a particular embodiment will depend on the constraints of the forces required to be exerted by the instrument 12 and the need to reduce the inertia and friction of the parts of the instrument that move during its actuation.

The surgical instrument of the present invention has also been illustrated as using drive motors M1, M2, M3, M4 and M5. This drive motors may be standard servo motors having position encoders as shown in FIG. 3. However, other actuators may be used, such as hydraulic actuators and piezoelectric motors. To be used as an actuator in the present surgical instrument a drive mechanism should be able to provide variable and controllable force and position control.

Figure 7:
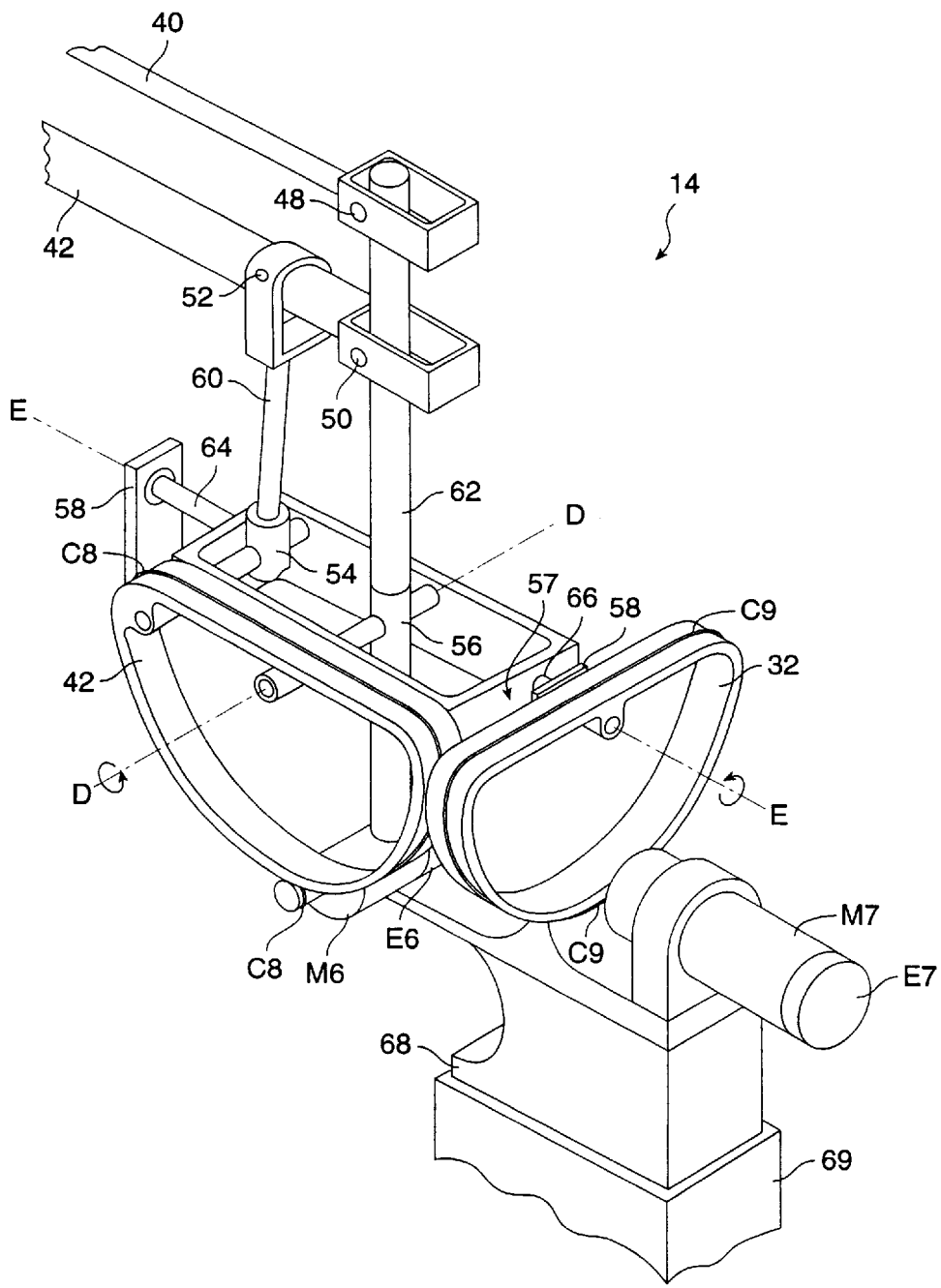
FIG. 7 is a perspective view of the base portion of the positioning mechanism showing the drive motors.

Referring to FIG. 7, the drive system of positioning mechanism 14 is now described in greater detail is mounted to base 68 which is mounted to the setup joint 69 (not shown). Positioning mechanism 14 includes drive motors M6 and M7. Drive motor M6 pivots positioning mechanism 14 about axis D—D with a range of approximately ±60°. Drive motor M7 pivots positioning mechanism about axis E—E with a range of approximately ±90°. Each drive motor M6 and M7 drives a respective cable C8 and C9 which is fixed to a respective drum 42 and 32. Drive motor M6 is mounted to member 62 and walks around the perimeter of drum 42 to rotate member 62 about axis D—D. Drive motor M7 is mounted to base 68 and remains stationary and walks around the perimeter of drum 32 to rotate positioning mechanism 14 about axis E—E. Shafts 64 and 66 extend from drum 42 and are coupled to ears 58 to allow rotation about axis E—E. Drum 32 is rigidly connected to shaft 66. Encoders E6 and E7 provide computer 11 with the rotational position of the drive shafts of respective drive motors M6 and M7.

Positioning mechanism 14 is preferably statically balanced such that the mass of the positioning mechanism 14 and instrument 12 is approximately symmetrically distributed about axis E—E. For example drive motor M6 is located under axis E—E to partially counterbalance the weight of links 40, 42, 60 and 62. Additional counterweights can be added without compromising force reflection because they add inertia to positioning mechanism 14 and not instrument 12. Static balancing may be facilitated by reducing the mass of the positioning mechanism by using lightweight materials such as aluminum tubing for construction of the links. Static balancing is advantageous because it reduces the balancing load that would otherwise be placed on drive motors M6 and M7. Moreover, static balancing is one means for reducing the chance for rapid motion of the positioning mechanism 14 and instrument 12 in the event of failure of either of drive motors M6 or M7.

Figure 8A:
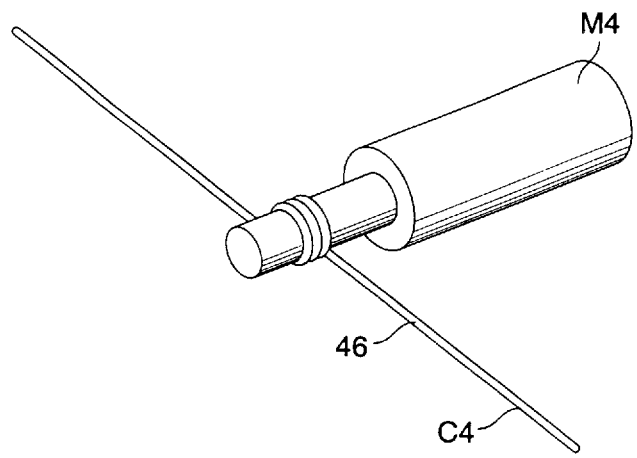
FIG. 8a is a perspective view of a cable wrapped around the drive shaft of a drive motor.
Figure 8B:
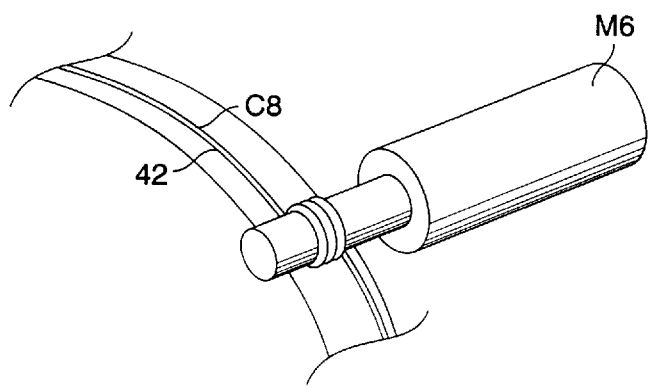
FIG. 8b is a perspective view of a cable wrapped around the drive shaft of a drive motor and driving a drum mechanism.

Referring to FIGS. 8a and 8b, cables C1, C2, C3, C4, C5, C8 and C9 are driven by being wrapped about the drive shaft of their respective drive motors M1, M2, M3, M4, M5, M6 and M7. For example, in FIG. 8a, cable C4 of cable loop 46 is wrapped around the drive shaft of motor M4. Cable C4 is preferably wrapped two times around the drive shaft to provide enough friction between the cable C4 and the drive shaft to prevent slippage. In order to further prevent slippage the cable may be fixed to the drive shaft at one point by soldering, welding or mechanical fixing means. However, in such an embodiment the range of motion of the cable is limited by the length of cable wrapped around the drive shaft or capstan thus several turns of cable are usually required.

FIG. 8b illustrates the cable drive for drums 32 and 42 of positioning mechanism 14. As the shaft of drive motor M6 rotates, cable C8 winds onto one side of the shaft and out from the other side. Thus, cable C8 translates past the shaft of motor M6 resulting in rotation of drum 42. Note that the shaft of motor M6 has no direct contact with the surface of drum 42.

Figure 8C:
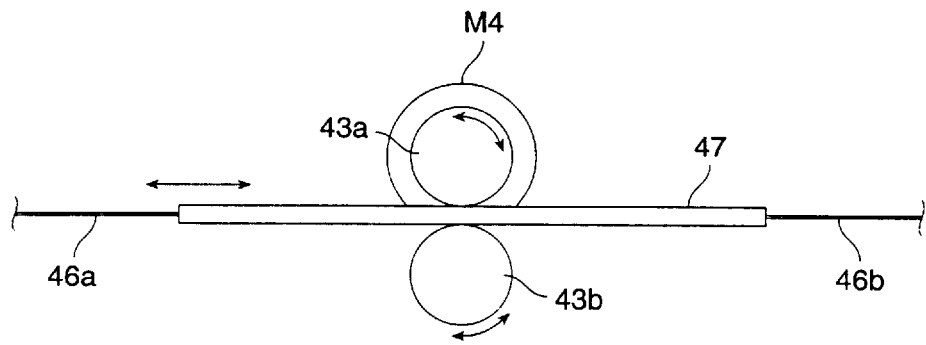
FIG. 8c is a schematic drawing showing another preferred method for driving the cables in the present invention.

FIG. 8c depicts another preferred method for driving cables. For example, motor M4 includes a drive wheel 43a and a idler wheel 43b for frictionally driving an elongate member 47 therebetween. Cable C4 consists of two halves, 46a and 46b which are fixed to opposite ends of member 47.

Figure 9:
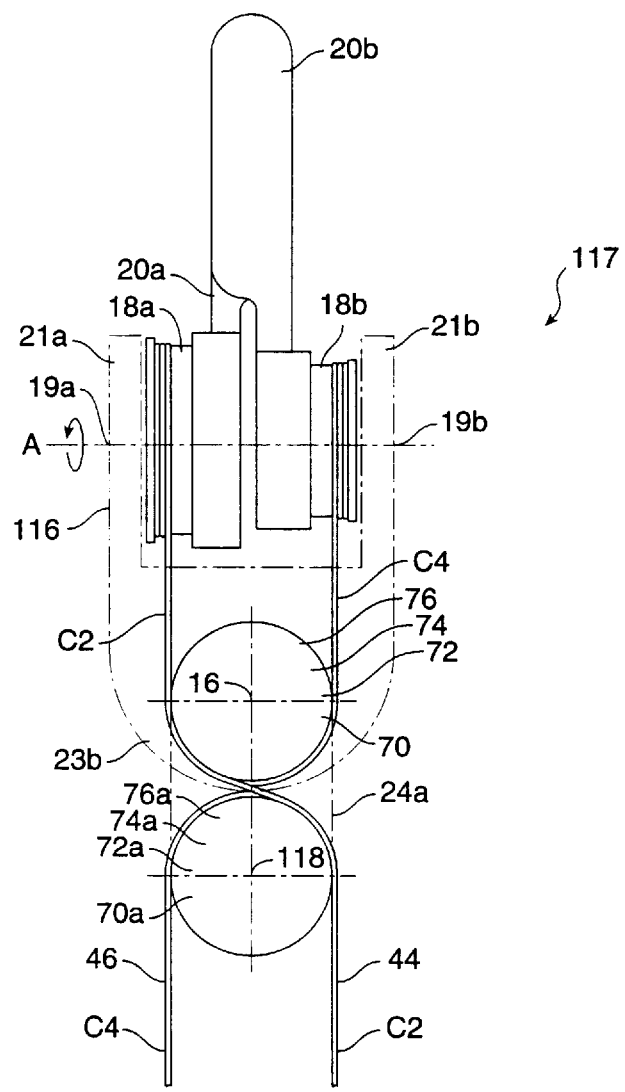
FIG. 9 is a top view of the wrist member of another preferred force-reflecting instrument.

FIG. 9 depicts the distal end and wrist member 116 of another preferred instrument 117. Instrument 117 differs from instrument 12 in that instrument 117 includes eight intermediate idler pulleys instead of four. Instrument 117 includes intermediate idler pulleys 76, 74, 72 and 70 at wrist joint 16 but also includes intermediate idler pulleys 76a, 74a, 72a and 70a which are positioned adjacent to idler pulleys 76, 74, 72 and 70 on tongue 24a along shaft 118. Cables C1, C2, C3 and C4 do not make a complete wrap around each intermediate idler pulley but instead only contact about 90° of the surface of each pulley. This prevents the cables from crossing each other and rubbing together which prevents friction and noise.

Figure 10:
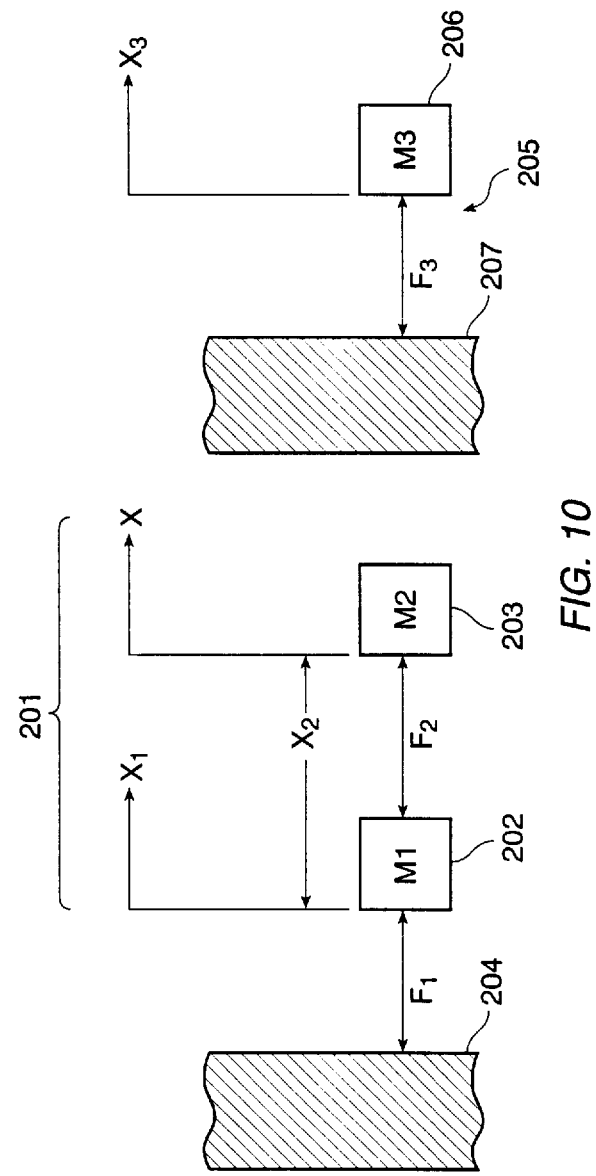
FIG. 10 is a schematic representation of a simple master-slave system for illustration purposes.

Referring to FIG. 10, the principle behind the macro-micro control of positioning mechanism 14 and instrument 12 is described. Macro-micro control takes advantage of the dynamics of the system to optimize force sensitivity by reducing the inertia measured at the output end of the slave system. In particular, it is often the case that distal degrees-of-freedom have a smaller range of motion than do proximal degrees-of-freedom. In our case, a small wrist mounted on the end of a laparoscopic instrument would correspond to a micro-instrument (the wrist) mounted on a macro-instrument (the positioning mechanism).

Macro-micro control, as defined here, is the use of two or more redundant degrees-of-freedom actuated in series, via an appropriate controller, for the purpose of reducing the effective inertia as measured from the distal side of the macro-micro system (the side which interacts with the patient) to approximate that of the micro-freedom while retaining the range of motion of the macro-freedom. The macro-freedom, defined to be the proximal side of the system, is actuated relative to ground and is typically large with a large range of motion and inertia. The micro-freedom is small with a correspondingly smaller range of motion and inertia, and is actuated with relative to the macro-freedom, and is defined to be the distal side of the system.

FIG. 10 depicts an example of a one degree-of-freedom master-slave system which consists of a linear slave instrument 201 operated by two redundant actuators 202, 203 and a linear master device 205 having one actuator 206. M3 is a mass representing a master device 205 which is used to control the motions of the slave device. F3 is the force applied to mass M3 by the master actuator 206. M1 is a mass representing the macro-instrument which has a large range of motion—it is equivalent to the positioning mechanism of the present invention. F1 is the force applied by the macro-actuator 202 to ground. The macro-instrument is slaved directly to the position of the master 205 and operates to maintain the micro-instrument within its workspace. In order to allow for a wide range of motion, the macro-instrument has a large structure and thus typically has a relatively high inertia and possibly high friction. However, the macro-instrument must still be able to maintain good (high bandwidth) position and velocity control.

M2 is a mass representing the micro-instrument which has a relatively small range of motion relative to the macro-instrument and the master 205. However, the small structure of the micro-instrument M2 enables it to be built to have low inertia and low friction compared to the macro-instrument. The slave degrees-of-freedom both contribute to the output X because the micro-instrument is mounted on the macro-instrument in serial fashion. The micro-instrument force, F2, is applied between M1 and M2. X1 is the position of the macro-instrument, and F1 is the motor force applied between the macro-instrument and ground 204 by the macro-actuator 202. X2 is the position of the micro-instrument relative to the macro-instrument. X is the position of the micro-instrument relative to ground resulting from the combination of X1 and X2. X3 is the position of the master instrument M3. The user who is holding the master M3 feels the resulting forces as force reflection.

The equations for controlling this representative macro-micro system are given below in which the subscript d denotes a desired value of a particular position or velocity. In the equations below, $k_{p1}$, $k_{p2}$ and $k_{p3}$ are position gains and $k_{v1}$, $k_{v2}$ and $k_{v3}$ are velocity gains. V is dX/dt, the velocity of the macro-micro instrument. V1 is dX1/dt, the velocity of the macro-instrument. Posscale is a scale factor used to scale motions between the master and the slave. For example, if posscale equals 1, a one cm master movement will result in a 1 cm slave movement. If posscale equals 2, a 1 cm master movement will result in a ½ cm slave movement.

| | |
|---|---|
| $X_d = X_3/\text{posscale}$ | Equation 1. |
| $V_d = V_3/\text{posscale}$ | Equation 2. |
| $X_{1d} = X_d$ | Equation 3. |
| $X_{2d} = X_d - X_1$ | Equation 4. |

$$X_{3d} = X.\text{posscale} \quad \text{Equation 5.}$$

$$V_{1d} = V_d \quad \text{Equation 6.}$$

$$V_{2d} = V_d - V_1 \quad \text{Equation 7.}$$

$$V_{3d} = V.\text{posscale} \quad \text{Equation 8.}$$

$$F_1 = -k_{p1}(X_1 - X_{1d}) - k_{v1}(V_1 - V_{1d}) \quad \text{Equation 9.}$$

$$F_2 = -k_{p2}(X_2 - X_{2d}) - k_{v2}(V_2 - V_{2d}) \quad \text{Equation 10.}$$

$$F_3 = -k_{p3}(X_3 - X_{3d}) - k_{v3}(V_3 - V_{3d}) \quad \text{Equation 11.}$$

The equations given above represent one specific implementation of macro-micro-control. Variations in the implementation may be necessary for the purpose of improving system stability. However, as can be determined from the above equations, both position and velocity gains affect system impedance and stability. Force and impedance scaling between the master and slave is achieved by changing the position gains $k_{p1}$, $k_{p2}$, and $k_{p3}$ and the factor posscale. In particular, the ratio $k_{p3}/k_{p2}$ determines the force gain between the master and slave. For example, when the ratio $k_{p3}/k_{p2} = 2$ forces applied to the slave are magnified to be twice as large at the master. If, in addition, posscale=1, the stiffness of objects at the slave will also be doubled at the master. If $k_{p3}/k_{p2} = 2$ and posscale=2, stiffness encountered by the slave will be unchanged at the master, while forces will still be doubled. The velocity gains $k_{v1}$, $k_{v2}$, and $k_{v3}$ can be used to control system stability.

To understand the qualitative effect of macro-micro control imagine that a small force is applied to M2. Because M2 has low inertia, and presumably also low fiction, it will deflect with little resistance relative to M1. This motion will be tracked by the master M3. If the user is holding M3, he will feel a force, and the sensitivity with which he will feel forces applied to M2 increases as the inertia and friction of M2 relative to M1 decreases. The utility of coupling M2 to M1 is that M1 increases the range of motion of the slave. Since M2 can only move a short distance relative to M1, M1 provides a moving base for M1, so that the combined system has both the sensitivity of M2 and the large range of motion of M1.

The macro-micro actuation scheme illustrated in FIG. 10 is a simple one degree-of-freedom linear system. However, the same scheme and the same general equations can be readily expanded to a 3 degree-of-freedom system such as applicants' system using well known principals of robotics and mathematics. The motion of the point $P_s$ of instrument 14 has only three possible degrees-of-freedom and is redundantly controlled by motion of the combination of the positioning mechanism and instrument with six degrees-of-freedom. For each axis of motion of the point PS there are a plurality of actuators which control motion of point along that axis. For each such axis under macro-micro control there is at least one micro-actuator and at least one macro-actuator distinct from the micro-actuator.

While this invention has been particularly shown and described with reference to preferred embodiments thereof, it will be understood by those skilled in the art that various changes in form and details may be made therein without departing from the spirit and scope of the invention as defined by the appended claims. Although the present invention has been described for performing laparoscopic surgery, other forms of endoscopic surgery as well as open surgery can also be performed. The present instrument can also be employed for any suitable remote controlled application requiring the a dexterous instrument with high quality force feedback. Possible applications include bomb disposal, handling of hazardous or radioactive materials, deep sea applications, outer space applications or other applications in inaccessible locations.

What is claimed is:

1. A system for minimally invasive surgery comprising an articulated surgical instrument, a positioning mechanism and a controller wherein:

the articulated surgical instrument is adapted to be inserted into a patient through a small incision to a location adjacent a surgical worksite and comprises a surgical end effector connected by a wrist mechanism to an elongate support member which is coupled to a mounting bracket wherein the mounting bracket is adapted to releasably connect the surgical instrument to the positioning mechanism and wherein the surgical instrument is operated by four actuators to move the end effector of the surgical instrument with four degrees-of-freedom relative to the mounting bracket;

the positioning mechanism comprises a base which is fixed relative to the patient, a support bracket adapted to releasably connect to the mounting bracket of the surgical instrument, and an arm linkage connecting the base to the support bracket wherein the arm linkage comprises a plurality of rigid links and joints and is operated by two actuators to move the support bracket with two degrees-of-freedom relative to the base whereby the combination of the positioning mechanism and the surgical instrument is operative to move the end effector of the surgical instrument with six degrees-of-freedom relative to the base;

wherein the surgical instrument provides force feedback to the controller in at least three degrees-of-freedom; and wherein the positioning mechanism provides no force feedback to the controller.

2. The system of claim 1 wherein the articulated surgical instrument and the positioning mechanism are operated together in accordance with a macro-micro actuation scheme.

3. The system of claim 1 wherein the positioning mechanism further comprises a setup joint which connects the base to an operating room table.

4. The system of claim 2 wherein force scaling is provided between the controller and the surgical instrument.

5. The system of claim 2 wherein forces incident on the surgical instrument are magnified at the controller.

6. The system of claim 2 wherein impedance scaling is provided between the controller and the surgical instrument.

7. The system of claim 4 wherein impedance scaling is provided between the controller and the surgical instrument.

8. A system for minimally invasive surgery comprising:

surgical manipulation means for insertion into a patient through a small incision to a location adjacent a surgical worksite and manipulation of human tissues at the surgical worksite;

positioning means for releasably supporting the surgical manipulation means and moving the surgical manipulation means with two degrees-of-freedom;

wherein the surgical manipulation means comprises a surgical end effector for manipulating human tissues, wherein the surgical manipulation means comprises an articulated wrist mechanism which couples the surgical end effector means to an elongate support member and permits movement of the surgical end effector with two degrees-of-freedom relative to the elongate support member;

wherein the surgical manipulation means further comprises one or more joints which couple the elongate support member to a mounting bracket such that the elongate support member can move with two degrees-of-freedom relative to the mounting bracket;

wherein the mounting bracket is adapted to releasably connect the surgical manipulation means to the positioning means;

whereby the combination of the positioning mechanism and the surgical instrument is operative to move the end effector of the surgical instrument with six degrees-of-freedom relative to the base;

wherein the surgical manipulation means provides force feedback to the controller means in at least three degrees-of-freedom; and wherein the positioning means provides no force feedback to the controller means.

9. The system of claim 8 wherein the surgical manipulation means and the positioning means operated together in accordance with a macro-micro actuation scheme.

10. The system of claim 8 wherein the positioning mechanism further comprises setup means for connecting the positioning means to an operating room table.

11. The system of claim 9 wherein force scaling is provided between the controller means and the surgical manipulation means.

12. The system of claim 10 wherein forces incident on the surgical manipulation means are magnified at the controller means.

13. The system of claim 9 wherein impedance scaling is provided between the controller means and the surgical manipulation means.

14. The system of claim 11 wherein impedance scaling is provided between the controller means and the surgical manipulation means.

15. A method for minimally invasive surgery comprising the steps of:

providing an articulated surgical instrument comprising a surgical end effector connected by a wrist mechanism to an elongate support member which is coupled to a mounting bracket wherein the mounting bracket is adapted to releasably connect the surgical instrument to the positioning mechanism;

providing a positioning mechanism comprising a base which is fixed relative to the patient, a support bracket adapted to releasably connect to the mounting bracket of the surgical instrument, and an arm linkage connecting the base to the support bracket wherein the arm linkage comprises a plurality of rigid links and joints;

coupling the surgical instrument to the positioning mechanism;

inserting the surgical instrument into a through a small incision to a location adjacent a surgical worksite;

operating a plurality of actuators to move the end effector of the surgical instrument with four degrees-of-freedom relative to the mounting bracket and move the support bracket of the positioning mechanism with two degrees-of-freedom relative to the base;

transmitting force feedback information from the surgical instrument to the controller in at least three degrees-of-freedom;

whereby the end effector of the surgical instrument is positioned with six degrees-of-freedom relative to the surgical worksite and force feedback control is provided in three degrees-of-freedom.

16. The method of claim 15 wherein the step of operating a plurality of actuators comprises operating the actuators in accordance with a macro-micro actuation scheme.

17. The method of claim 15 further comprising the steps of providing a setup joint; connecting the setup joint to the base of the positioning mechanism and to an operating room table.

18. The method of claim 16 wherein the step of operating a plurality of actuators comprises operating the actuators to provide force scaling between the controller and the surgical instrument.

19. The method of claim 18 wherein the step of operating a plurality of actuators comprises operating the actuators to magnify forces incident on the surgical instrument at the controller.

20. The system of claim 16 wherein the step of operating a plurality of actuators comprises operating the actuators to provide impedance scaling between the controller and the surgical instrument.

21. The system of claim 18 wherein the step of operating a plurality of actuators comprises operating the actuators to provide impedance scaling between the controller and the surgical instrument.

* * * * *